US00PP35527P2

(12) United States Plant Patent
Hansen

(10) Patent No.: US PP35,527 P2
(45) Date of Patent: Dec. 5, 2023

(54) **X *MANGAVE* PLANT NAMED 'NIAGARA FALLS'**

(50) Latin Name: ***Manfreda* times *Agave***
Varietal Denomination: Niagara Falls

(71) Applicant: Hans A Hansen, Zeeland, MI (US)

(72) Inventor: Hans A Hansen, Zeeland, MI (US)

(73) Assignee: Walters Gardens Inc., Zeeland, MI (US)

( * ) Notice: Subject to any disclaimer, the term of this patent is extended or adjusted under 35 U.S.C. 154(b) by 0 days.

(21) Appl. No.: 18/445,127

(22) Filed: Apr. 17, 2023

(51) Int. Cl.
*A01H 5/12* (2018.01)
*A01H 6/00* (2018.01)

(52) U.S. Cl.
USPC ..... Plt./373

(58) Field of Classification Search
USPC ..... Plt./373
See application file for complete search history.

*Primary Examiner* — Karen M Redden

(57) ABSTRACT

A new and unique x *Mangave* plant named 'Niagara Falls' characterized by a medium to large mound of broadly lanceolate, fleshy, longitudinally-folded, dark green foliage having a broad yellowish-chartreuse margin and chartreuse intermediate zone. The leaves cascade or arch downward toward the tips with maturity. Foliage displays spots of purplish-red color in high ultraviolet exposure mainly concentrated near the leaf base. Leaves are deeply scalloped with medium-sized teeth. The new plant is suitable for the garden or as a potted plant in the garden or home.

1 Drawing Sheet

Botanical classification: Hybrid, *Manfreda* times *Agave*, known as x *Mangave*.
Variety denomination: 'Niagara Falls'.

STATEMENT REGARDING PRIOR DISCLOSURES UNDER 37 CFR 1.77(b)(6)

No plants of x *Mangave* 'Niagara Falls' have been sold, in this country or anywhere in the world, nor has any disclosure of the new plant been made public prior to the filing of this application.

BACKGROUND OF THE INVENTION

The present invention relates to the new and distinct x *Mangave* hybrid plant, x *Mangave* 'Niagara Falls' discovered by the inventor at a wholesale perennial nursery in Zeeland, Michigan, USA as an uninduced whole plant mutation of x *Mangave* 'Falling Waters' U.S. Plant Pat. No. 30,650 on Oct. 4, 2019. Through trials at the same nursery, the plant was assigned the breeder code 19-SP-MANG-894. The new plant has been successfully asexually propagated by sterile shoot-tip tissue culture at the same nursery in Zeeland, Michigan, and has been found to produce stable and identical plants that maintain all the unique characteristics of the original plant.

No plants of x *Mangave* 'Niagara Falls' have been sold, under this or any name, in this country or anywhere in the world, prior to the filing of this application, nor has any disclosure of the new plant been made prior to the filing of this application.

BRIEF SUMMARY OF THE INVENTION

X *Mangave* 'Niagara Falls' differs from its parent as well as all other *Manfreda, Agave* and x *Mangave* known to the applicant. The new plant has leaf variegation with margins of yellowish-chartreuse.

The nearest comparison plants are: x *Mangave* 'Bridal Falls' U.S. Plant Pat. No. 33,080, 'Pineapple Punch' U.S. Plant Pat. No. 32,041, 'Kaleidoscope' U.S. Plant Pat. No. 28,614, 'Foxy Lady' U.S. Plant Pat. No. 33,032, 'Navajo Princess' U.S. Plant Pat. No. 31,136, and 'Snow Leopard' U.S. Plant Pat. No. 31,137.

'Bridal Falls' has a similar habit and foliage size, but the margin is creamy-white and the intermediate zone is minty-green. 'Pineapple Punch' has shorter flatter leaves with smaller marginal teeth. 'Kaleidoscope' has longer leaves with blue-green centers and variegated yellowish-green to yellowish-cream margins. The foliage of 'Foxy Lady' has foliage that is flatter, shorter, and more glaucous, producing a silvery color with more lavender undertones, and the marginal teeth are closer together, with a creamy-white color and have an orangish-brown coloration to the tips. 'Navajo Princess' and 'Snow Leopard' are both variegated with creamy-white margins but the foliage is longer, flatter, and with smaller marginal teeth. Compared with 'Whale Shark' U.S. Plant Patent Application copending the new plant has a dark green leaf center, larger marginal teeth, and the foliage is more longitudinally folded. 'Falling Waters' differs in not having the leaf variegation with margins of yellowish-chartreuse and the intermediate zone between the margin and the dark green leaf center.

The new plant, 'Niagara Falls', is unique from all of the above-listed cultivars, and all *Agave*, x *Mangave*, and *Manfreda* known to the inventor by the following combined traits:

1. Medium to large mound of lanceolate, broad, fleshy, longitudinally-folded foliage;
2. Leaf margins are yellowish-chartreuse with a chartreuse zone between the margin and the dark-green leaf center;
3. Foliage has faint spots that become more pronounced purplish-red color in strong ultraviolet light;

4. Leaf margins deeply scalloped with medium-sized teeth;
5. Moderate growth rate.
6. Foliage cascades or arches with age.

BRIEF DESCRIPTION OF THE DRAWING

The photograph of x *Mangave* 'Niagara Falls' demonstrates the overall appearance of the new plant including the unique traits of a three-year-old plant grown in a container in a partially-shaded greenhouse with supplemental water and fertilizer as needed. The colors are as accurate as reasonably possible with color reproductions. Ambient light spectrum, temperature, source, and direction may cause the appearance of minor variations in color.

DETAILED BOTANICAL DESCRIPTION

Figure 1:
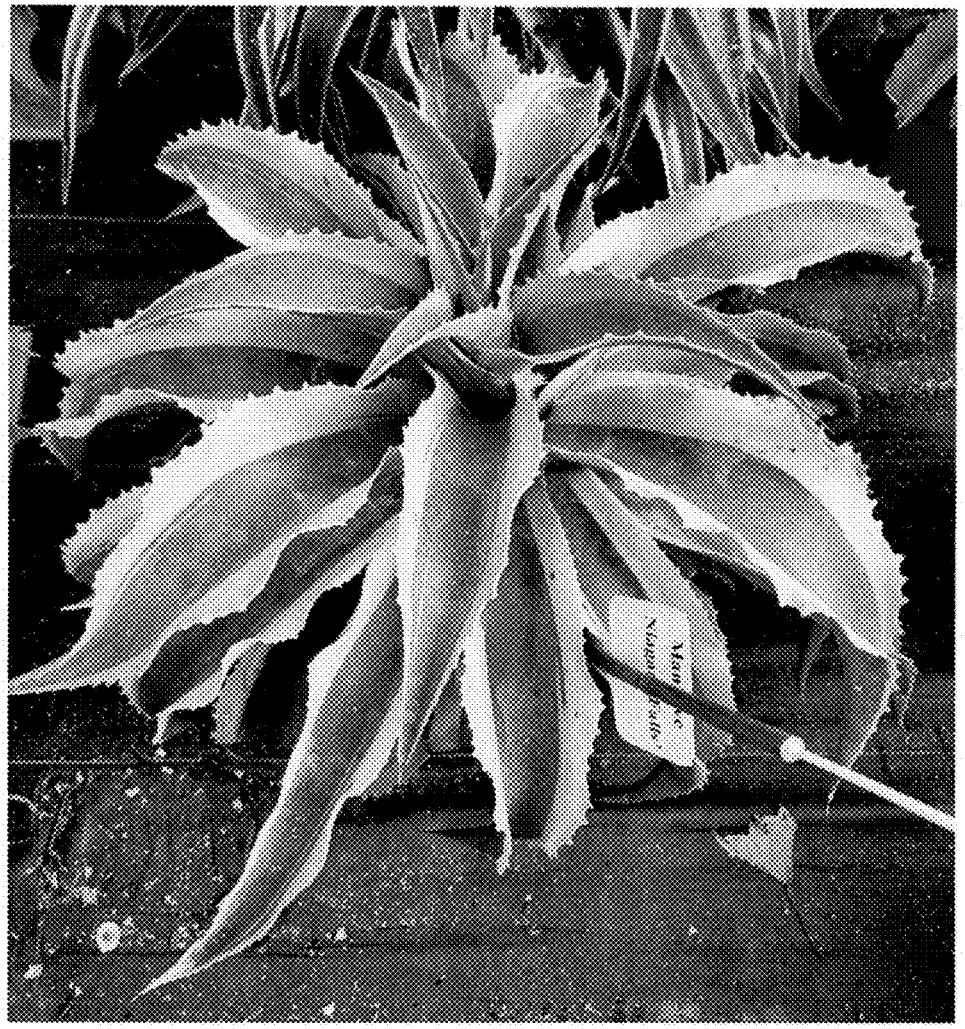
FIG. 1 shows the habit of the new plant habit.
Figure 2:
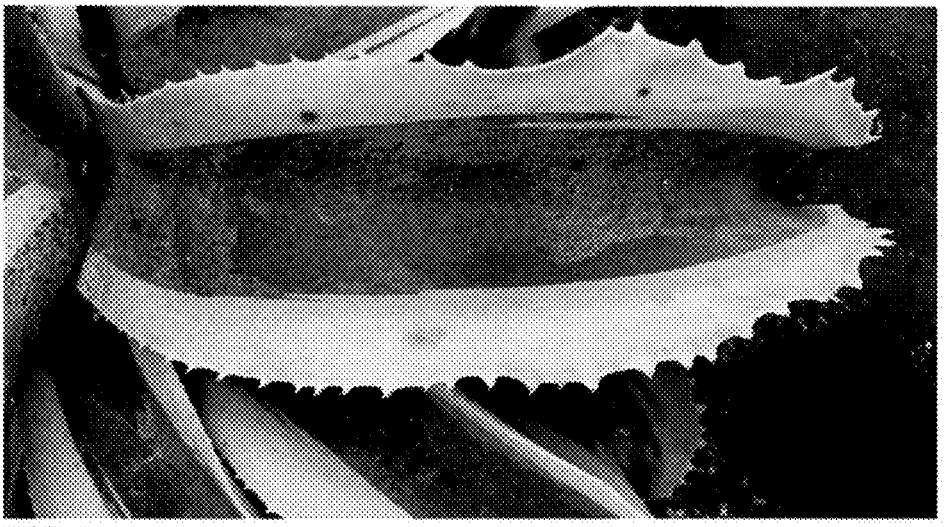
FIG. 2 shows a close-up of the variegation of the leaves and the marginal teeth.

The following descriptions and color references are based on the 2015 edition of The Royal Horticultural Society Colour Chart except where common dictionary terms are used. The new plant, x *Mangave* 'Niagara Falls', has not been observed under all possible environments. The phenotype may vary slightly with different environmental conditions, such as temperature, light, fertility, moisture, and maturity levels, but without any change in the genotype. The following observations and size descriptions are of a three-year-old plant in a partially-shaded, commercial, wholesale greenhouse in Zeeland, Michigan with supplemental water and fertilizer as needed.

Parentage: An uninduced mutation of x *Mangave* 'Falling Waters' as the parent.

Propagation: Core removal of meristem and by sterile shoot-tip tissue culture.

Time to initiate roots from tissue culture: About 21 days.

Growth rate: Moderate.

Crop time: About 12 to 16 weeks to finish in a 3.8-liter container from a 35 mm tissue culture growing at about 21° C.

Rooting habit: Fleshy, lightly branching, with roots up to 18 cm long.

Root color: Nearest RHS 158C.

Plant shape and habit: Succulent herbaceous perennial with basal rosettes of about 47 leaves radially emerging outwardly from central stem, producing a radially-symmetrical, rounded mound.

Plant size: Foliage height about 28 cm tall from soil line to the top of the leaves and about 73 cm wide at the widest point slightly below soil line in container.

Foliage description: Lanceolate; simple; sessile; bi-laterally symmetrical; apex acute with apical spine; apical spine firm, sharp, to about 15 mm long; base truncate; conduplicate, especially young distal leaves; margins coarsely irregularly dentate; slightly glaucous waxy bloom abaxial and adaxial; without trichomes; with abaxial and adaxial spots about 2 mm to 3 mm long and wide, rarely touching or overlapping.

Teeth: Sharp; initially flexible, apex becoming harder with age; apex about 1 mm long and 1 mm long on protrusion to about 4 mm long and about 4 mm wide at base; average about 8 mm apart on mature leaves.

Leaf size: To about 40 cm long, about 9.5 cm wide toward base; and about 6 mm thick at base; average about 32 cm long, 8.5 cm wide and 5 mm thick; adaxial margin to about 31 mm wide, center to about 60 mm wide and intermediate zone to about 15 mm wide; abaxial margin to about 25 mm wide, center to about 68 cm wide and intermediate zone to about 6 mm wide.

Foliage fragrance: None observed.

Leaf number: About 47 per plant.

Leaf blade color:

*Adaxial* (*young*).—Center between RHS NN137C and RHS NN137B with spots nearest RHS NN137A in low ultraviolet light and nearest RHS 187A in high ultraviolet light; margin and marginal teeth between RHS 147C and RHS 147B with spots between RHS 187C and RHS 187B; intermediate zone between margin and center not obvious in young leaves.

*Abaxial* (*young*).—Center between RHS 194B and RHS 196A with spots not obvious; margin and marginal teeth nearest RHS 11B with spots a faint blush or nearest RHS 186A; intermediate zone not obvious.

*Adaxial* (*older*).—Center nearest RHS 137A with spots nearest RHS NN137A with lower ultraviolet exposure and toward base of leaf nearest RHS 187C; margin and teeth variable, nearest RHS 7B and nearest RHS 146C with spots mainly proximally and obvious only with higher ultraviolet exposure a faint blush between RHS 186A and RHS 187C, and 1 mm apex nearest RHS 200B; intermediate zone variable nearest RHS 148C and between RHS 153D and RHS 160D and with higher ultraviolet exposure spots mainly proximally between RHS 186A and RHS 187C.

*Abaxial* (*older*).—Center nearest RHS N138B with spots mainly proximally between RHS 187A and RHS N187A; margin and teeth variable, nearest RHS 7B and nearest RHS 146C with spots mainly proximally and obvious only with higher ultraviolet exposure a faint blush between RHS 186A and RHS 187C, and 1 mm apex nearest RHS 200B; intermediate zone between RHS 148C and RHS 160C with spots not obvious; Adaxial and abaxial surfaces also occasionally displaying random streaks with the margin color breaching into the center or intermediate zone and from the center breaching into the margin or intermediate zone.

Apical spine: On young leaves between RHS 166B and RHS N163A, on older leaves to nearest RHS 166A.

Petiole: Leaves sessile.

Veins: Parallel; not distinct abaxial or adaxial.

Flower description: Not yet observed to date.

Fruit and seed not observed to date.

Disease resistance: x *Mangave* 'Niagara Falls' has not been observed to be resistant to diseases beyond that which is normal for x *Mangave, Agave* or *Manfreda*. The new plant is xeromorphic and survives well with minimal water once established. The new plant is estimated to be hardy at least from USDA zone 7b. The full extent of winter hardiness has not been tested.

It is claimed:

1. A new and distinct cultivar of ornamental x *Mangave* plant named 'Niagara Falls' as herein described and illustrated.

* * * * *